US008020555B2

(12) United States Patent
Rapoport

(10) Patent No.: US 8,020,555 B2
(45) Date of Patent: Sep. 20, 2011

(54) SYSTEM AND METHOD FOR IMPROVED TREATMENT OF SLEEPING DISORDERS USING THERAPEUTIC POSITIVE AIRWAY PRESSURE

(75) Inventor: David M. Rapoport, New York, NY (US)

(73) Assignee: New York University, New York, NY (US)

( * ) Notice: Subject to any disclaimer, the term of this patent is extended or adjusted under 35 U.S.C. 154(b) by 2059 days.

(21) Appl. No.: 10/464,126

(22) Filed: Jun. 18, 2003

(65) Prior Publication Data
US 2004/0255942 A1 Dec. 23, 2004

(51) Int. Cl.
*A61M 16/00* (2006.01)
(52) U.S. Cl. .............................. 128/204.21; 128/204.23
(58) Field of Classification Search ............. 128/204.18, 128/204.21, 204.22, 204.23
See application file for complete search history.

(56) References Cited

U.S. PATENT DOCUMENTS

| | | |
|---|---|---|
| 4,655,213 A | 4/1987 | Rapoport et al. |
| 5,065,756 A | 11/1991 | Rapoport |
| 5,245,995 A | 9/1993 | Sullivan et al. |
| 5,335,654 A | 8/1994 | Rapoport |
| 5,433,193 A | 7/1995 | Sanders et al. |
| 5,490,502 A | 2/1996 | Rapoport et al. |
| 5,535,739 A | 7/1996 | Rapoport et al. |
| 5,546,933 A | 8/1996 | Rapoport et al. |
| 5,551,419 A | 9/1996 | Froehlich et al. |
| RE35,339 E | 10/1996 | Rapoport |
| 5,645,053 A | 7/1997 | Remmers et al. |
| 5,740,795 A | 4/1998 | Brydon |
| 5,803,066 A | 9/1998 | Rapoport et al. |
| 5,884,622 A * | 3/1999 | Younes ................. 128/204.21 |
| 5,953,713 A | 9/1999 | Behbehani et al. |
| 6,015,388 A | 1/2000 | Sackner et al. |
| 6,105,575 A | 8/2000 | Estes et al. |
| 6,135,106 A | 10/2000 | Dirks et al. |
| 6,142,952 A | 11/2000 | Behbehani et al. |

(Continued)

FOREIGN PATENT DOCUMENTS
EP 1 129 742 9/2001
(Continued)

OTHER PUBLICATIONS

"Economic Implications of the Diagnosis of Obstructive Sleep Apnea," Annuals of Internal Medicine, vol. 130, No. 6, pp. 533-534 (Mar. 16, 1999).

(Continued)

*Primary Examiner* — Danton DeMille
(74) *Attorney, Agent, or Firm* — Fay Kaplun & Marcin, LLP

(57) ABSTRACT

Described is a method and system providing therapeutic positive airway pressure to a particular area of patient's airways. The system may include a flow generator and a processing arrangement. The flow generator supplies an airflow to an airway of the patient. The processing arrangement is connected to the flow generator to control a supply pressure at which the airflow is generated by the flow generator. The processing arrangement continuously adjusts the supply pressure to maintain a pressure in a predetermined portion of the patent's airway substantially constant. The predetermined portion of the patient's airway includes a collapsible portion of an upper airway of the patient. The processing arrangement also controls the supply pressure to maintain the pressure in the collapsible portion of the patient's airway at a value at least as great as a tissue pressure below which the collapsible portion collapses.

22 Claims, 5 Drawing Sheets

U.S. PATENT DOCUMENTS

| | | | |
|---|---|---|---|
| 6,165,133 | A | 12/2000 | Rapoport et al. |
| 6,192,886 | B1 | 2/2001 | Rudolph |
| 6,286,508 | B1 | 9/2001 | Remmers et al. |
| 6,299,581 | B1 | 10/2001 | Rapoport et al. |
| 6,349,724 | B1 | 2/2002 | Burton et al. |
| 6,360,741 | B2 | 3/2002 | Truschel |
| 6,363,933 | B1 * | 4/2002 | Berthon-Jones ......... 128/204.23 |
| 6,371,112 | B1 | 4/2002 | Bibi |
| 6,397,845 | B1 | 6/2002 | Burton |
| 6,398,739 | B1 | 6/2002 | Sullivan et al. |
| 6,425,395 | B1 | 7/2002 | Brewer et al. |
| 6,427,689 | B1 | 8/2002 | Estes et al. |
| 6,488,634 | B1 | 12/2002 | Rapoport et al. |
| 6,530,372 | B1 * | 3/2003 | Madaus et al. ........... 128/204.23 |
| 6,550,478 | B2 * | 4/2003 | Remmers et al. ........ 128/204.18 |
| 6,609,517 | B1 * | 8/2003 | Estes et al. ............... 128/204.23 |
| 6,688,307 | B2 * | 2/2004 | Berthon-Jones ......... 128/204.21 |
| 2002/0014241 | A1 | 2/2002 | Gradon et al. |
| 2002/0023645 | A1 | 2/2002 | Zdrojkowski et al. |
| 2002/0096173 | A1 | 7/2002 | Berthon-Jones et al. |
| 2003/0000528 | A1 | 1/2003 | Eklund et al. |

FOREIGN PATENT DOCUMENTS

FR    2 663 547    12/1991

OTHER PUBLICATIONS

Fletcher et al., "Unattended Home Diagnosis and Treatment of Obstructive Sleep Apnea Without Polysomnography." Arch Fam Med, vol. 9, pp. 168-174 (Feb. 2000).

"Assessment and Management of Obstructive Sleep Apnea in Adults," Guidles & Protocols, Advisory Committee, British Columbia Medical Association, Ministry of Heath and Ministry Responsible for Seniors, pp. 1-4 (Revised 2000).

Goodday et al., "Obstructive Sleep Apnea Syndrome: Diagnosis and Management" Journal of the Canadian Dental Association, vol. 67, No. 11, pp. 652-659 (Dec. 2001).

* cited by examiner

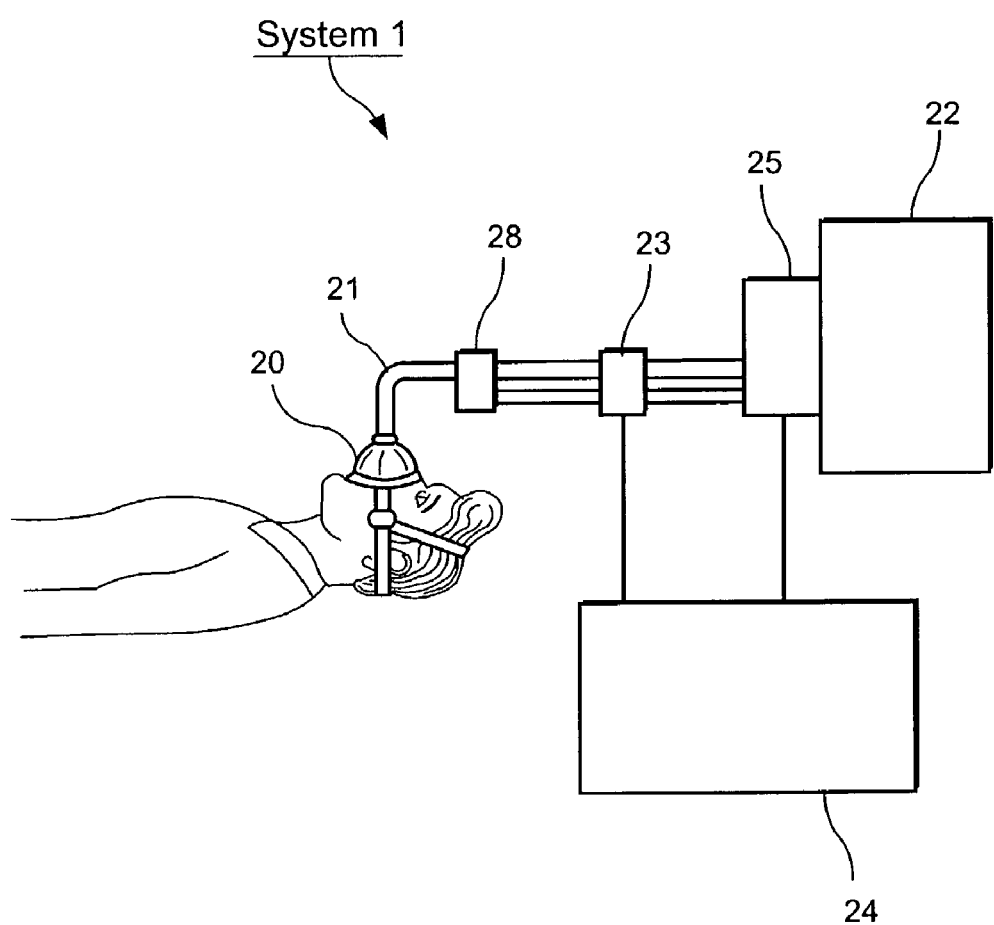
F I G. 1

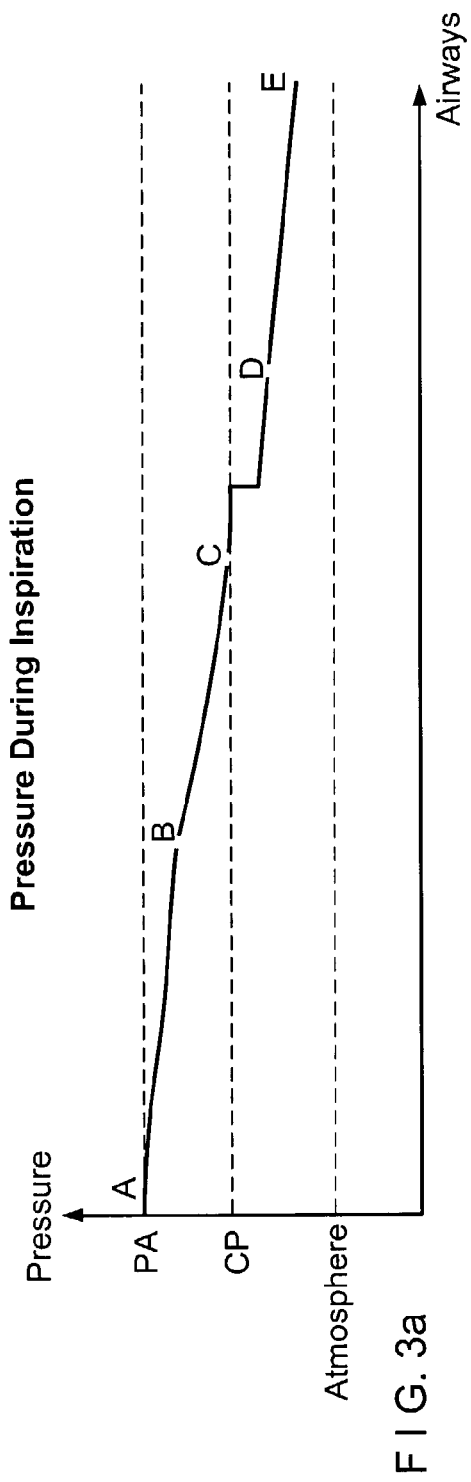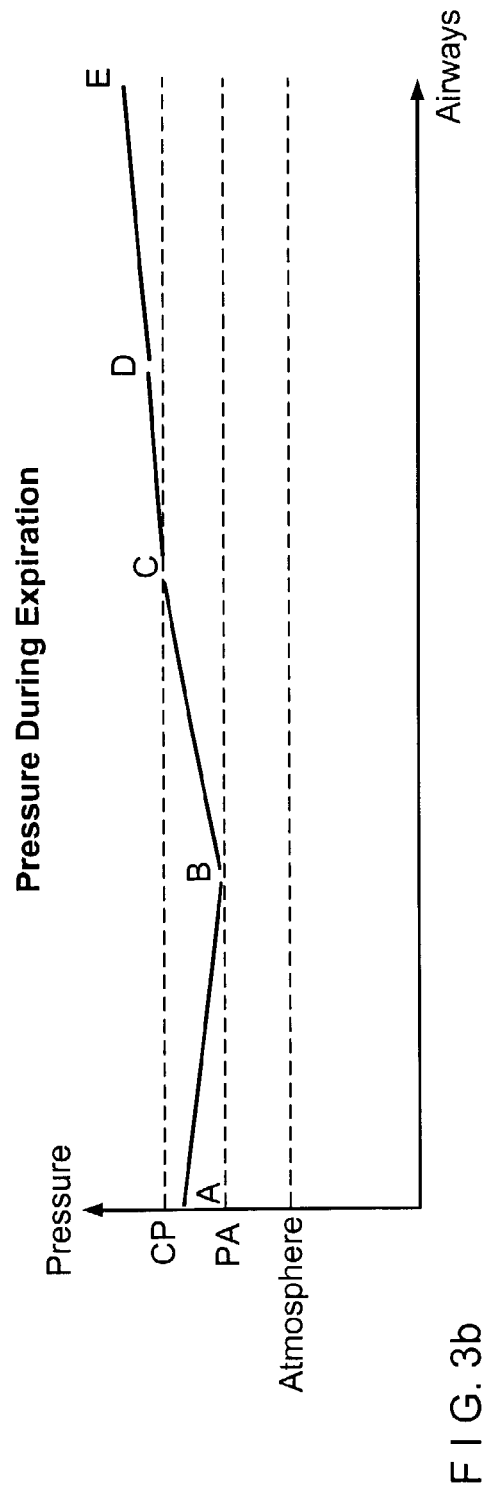
F I G. 3a
F I G. 3b

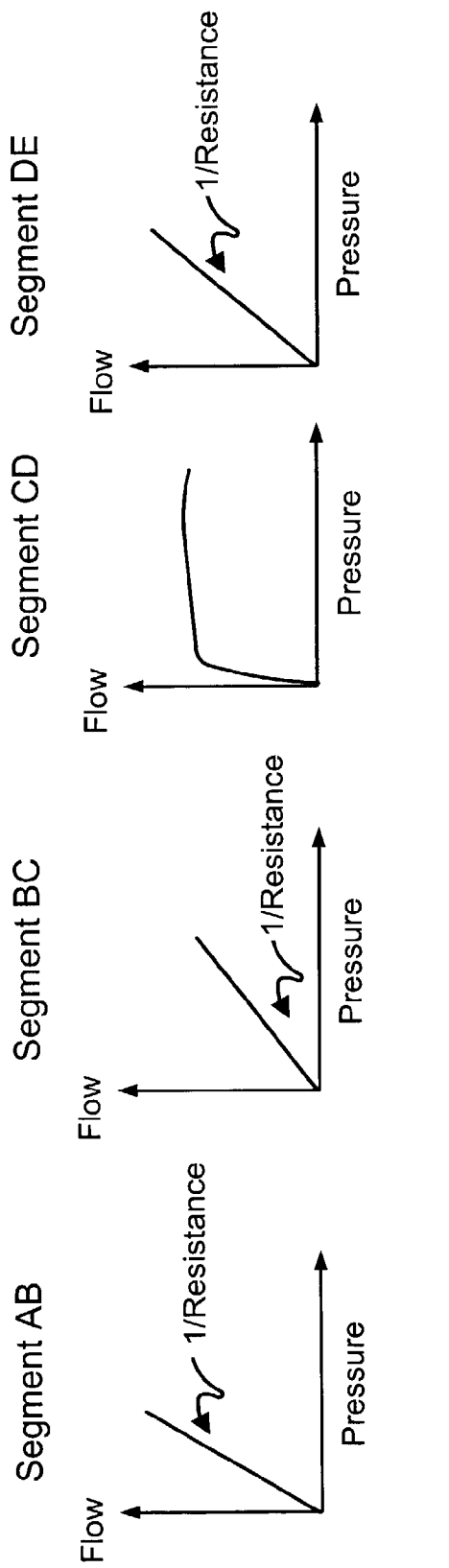

SYSTEM AND METHOD FOR IMPROVED TREATMENT OF SLEEPING DISORDERS USING THERAPEUTIC POSITIVE AIRWAY PRESSURE

BACKGROUND

Obstructive sleep apnea/hypopnea syndrome (OSAHS) is a well recognized disorder which may affect as much as 1-5% of the adult population. OSAHS is one of the most common causes of excessive daytime somnolence. OSAHS is most frequent in obese males, and it is the single most frequent reason for referral to sleep disorder clinics.

OSAHS is associated with all conditions in which there is anatomic or functional narrowing of the patient's upper airway, and is characterized by an intermittent obstruction of the upper airway occurring during sleep. The obstruction results in a spectrum of respiratory disturbances ranging from the total absence of airflow (apnea) to significant obstruction with or without reduced airflow (hypopnea, episodes of elevated upper airway resistance and snoring), despite continued respiratory efforts. The morbidity of the syndrome arises from hypoxemia, hypercapnia, bradycardia and sleep disruption associated with the respiratory obstruction event and arousals from sleep.

The pathophysiology of OSAHS is not fully worked out. However, it is now well recognized that obstruction of the upper airway during sleep is in part due to the collapsible behavior of the supraglottic segment of the respiratory airway during the negative intraluminal pressure generated by inspiratory effort. Thus, the human upper airway during sleep behaves as a Starling resistor, which is defined by the property that the flow is limited to a fixed value irrespective of the driving (inspiratory) pressure. Partial or complete airway collapse can then occur associated with the loss of airway tone which is characteristic of the onset of sleep and which may be exaggerated in OSAHS.

Since 1981, positive airway pressure (PAP) applied by a tight fitting nasal mask worn during sleep has evolved as the most effective treatment for this disorder, and is now the standard of care. The availability of this non-invasive form of therapy has resulted in extensive publicity for sleep apnea/hypopnea and the appearance of large numbers of patients who previously may have avoided the medical establishment because of the fear of tracheostomy. Increasing the comfort of the system (e.g., by minimizing the applied nasal pressure) has been a major goal of research aimed at improving patient compliance with therapy.

PAP therapy has become the mainstay of treatment in Obstructive Sleep Disordered Breathing (OSDB), which includes Obstructive Sleep Apnea/Hypopnea, Upper Airway Resistance Syndrome, Snoring, exaggerations of sleep induced rises in collapsibility of the upper airway and all conditions in which inappropriate collapsing of a segment of the upper airway causes significant un-physiologic obstruction to airflow. This collapse generally occurs whenever pressure in the collapsible portion of the airway becomes subatmospheric (or more accurately lower than a "tissue pressure" in the surrounding wall at a critical location in the upper airway of the patient). PAP therapy is directed to maintaining pressure in the collapsible portion of the airway at or above the critical "tissue pressure" at all times. In conventional CPAP, this is achieved by raising the airway pressure in the entire respiratory system to a level higher than this critical pressure.

Conventional implementations of PAP therapies have either provided a single continuous pressure at the nose or a combination of such a continuous pressure with a lowering of pressure when the pressure is not thought to be needed (e.g., during expiration). Continuous PAP ("CPAP") generally provides a constant pressure at least as large as the largest pressure necessary to prevent airway collapse. Some PAP therapies have provided and modified pressure profiles in an attempt to achieve the lowest (and presumably most comfortable) pressure which produces the desired therapeutic results.

For example, a procedure known as Bi-Level PAP is a known modification to CPAP. In Bi-Level PAP, a first constant pressure is set as an inspiratory pressure and a second lower constant pressure is set to be applied during expiration. The choice of the second pressure was originally based on the assumption that collapse of the upper airway occurs primarily during inspiration and that little or no collapsing force is generated absent the negative airway pressure generated during inspiration. However, Bi-level PAP has been shown to have little benefit in obstructive sleep apnea as the second expiratory pressure needs to be set at or near the level that would have been chosen for single pressure CPAP in order to prevent airway collapse. Bi-Level PAP is now generally restricted to patients who benefit from an unintended side effect of this mode of positive pressure (i.e., assisted ventilation that may arise when the difference between inspiration and expiration pressures are significant). However, as will be discussed below, patients who do not need assistance in breathing may find it difficult to draw the amount of air they desire as these systems react to their breathing by changing inhalation and exhalation pressures, and thus may not deliver the necessary pressure at the beginning of inspiration predictably.

Another modification of PAP is described, e.g., in U.S. Pat. No. 6,105,575. This PAP system provides to a patient a minimally sufficient pressure during at least a portion of a breathing cycle to perform at least one of the following functions at any given moment: (1) reduce cardiac preload and afterload and (2) prevent airway collapse. When operating to prevent airway collapse, the minimally sufficient pressure is determined by a summation of a pressure needed to prevent airway collapse and a pressure needed to overcome respiratory effort. This requirement to overcome respiratory pressure makes the system provide assisted ventilation, which, like Bi-Level PAP, is not need to treat obstructive sleep disordered breathing if there is no hypoventilation syndrome.

SUMMARY OF THE INVENTION

Described is a method and system providing therapeutic positive airway pressure designed to be held constant at a particular area of patient's airways. The system may include a flow generator and a processing arrangement. The flow generator supplies an airflow to an airway of the patient. The processing arrangement is connected to the flow generator to control a supply pressure at which the airflow is generated by the flow generator.

The processing arrangement continuously adjusts the supply pressure to maintain a pressure in a predetermined portion of the patent's airway substantially constant. The predetermined portion of the patient's airway includes a collapsible portion of an upper airway of the patient. The processing arrangement also controls the supply pressure to maintain the pressure in the collapsible portion of the patient's airway at a value at least as great as a tissue pressure below which the collapsible portion collapses.

BRIEF DESCRIPTION OF THE DRAWINGS

The accompanying drawings which are incorporated in and constitute part of the specification, illustrate several embodiments of the invention and, together with the description, serve to explain examples of the present invention. In the drawings:

FIG. 1 shows an exemplary embodiment of a system according to the present invention;

FIG. 3a illustrates a graph of pressure gradients during a positive airway pressure applied during inspiration;

FIG. 3b illustrates a graph of pressure gradients during a positive airway pressure applied during expiration;

FIGS. 4a-4d illustrate graphs of airflow/pressure relationships in a plurality of airway segments during utilization of the system according to the present invention.

DETAILED DESCRIPTION

Figure 2A:
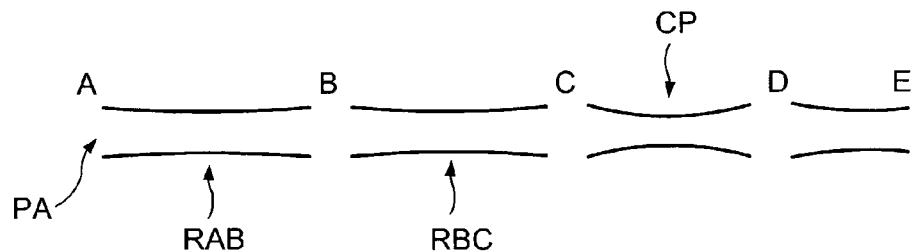
FIGS. 2a and 2b show a schematic airflow passage in the system illustrated in FIG. 1.

FIG. 1 shows an exemplary embodiment of a system 1 according to the present invention. The system 1 may include a mask 20 which is connected via a tube 21 to receive air from a flow generator 22. The mask 20 may cover patient's nose and/or mouth. A conventional flow and pressure sensor 23 is coupled to the tube 21 and detects both the airflow and pressure in the tube 21. Signals corresponding to the airflow and the pressure are provided to a processing arrangement 24 for processing. The processing arrangement 24 outputs a signal to a conventional flow control device 25 to control a pressure applied to the flow tube 21. Those skilled in the art will understand that, for certain types of flow generators which may by employed as the flow generator 22, the processing arrangement 24 may directly control the flow generator 22, instead of controlling airflow therefrom by manipulating the separate flow control device 25.

The system 1 also includes a conventional venting arrangement 28 which may be in the form of a leak port or a non-rebreathing valve with a venting tube. The venting arrangement 28 allows for gases exhaled by the patient to be diverted from the incoming air to prevent re-breathing of the exhaled gases.

Figure 2B:
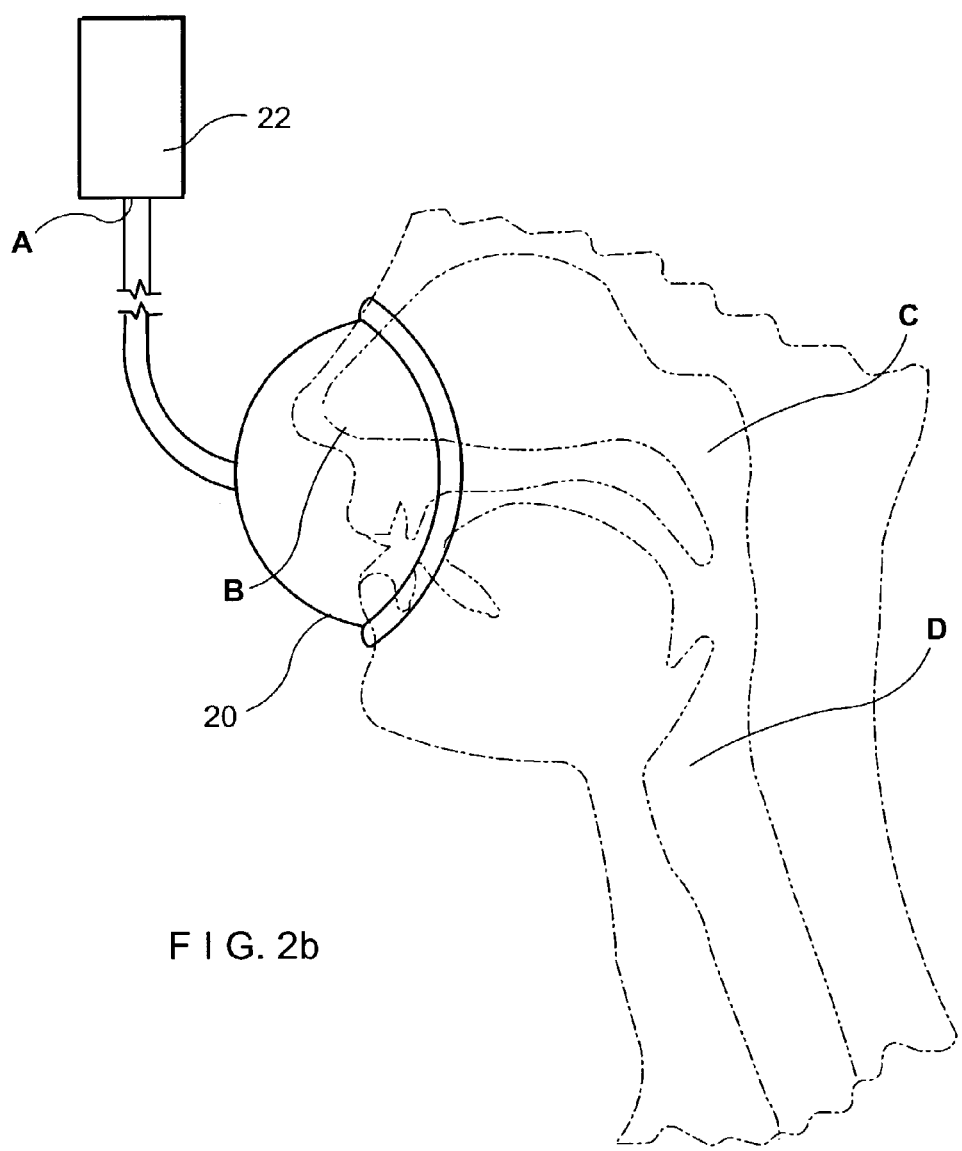

FIG. 2a shows a schematic of the airflow passage in the system 1 from the flow generator 22 to the lungs of the patient. In particular, the airflow passage may be divided into four logical segments AB, BC, CD and DE as illustrated in FIGS. 2a and 2b. First, the segment AB of the airflow passage extends from the flow generator 22 to the inlet of the patient's nose and include the tube 21 and the mask 20. A pressure $P_A$ is applied by the flow generator 22 to a front end of the segment AB.

The segments BC and CD comprise the upper airway of the patient extending between the patient's nose and a lower airway. In particular, the segment BC extends from the nose of the patient to the end of the area of the airway which has a boney support (i.e., extending through the nasopharynx to the end of the hard palate). The segment CD extends from the beginning of the unsupported airway (e.g., at or near the level of the soft palate) to the resumption of the non-collapsible airway (i.e., the segment DE), such as an entrance to the larynx. The segment BC is a non-collapsible segment of the upper airway, while the segment CD is a collapsible segment of the upper airway. Behavior of the segment CD is generally believed to be responsible for OSAHS. Finally, the segment DE is the lower airway of the patient and is located between the end of the upper airway (i.e., the larynx) and the alveoli of the lungs of the patient.

Figure 5A:
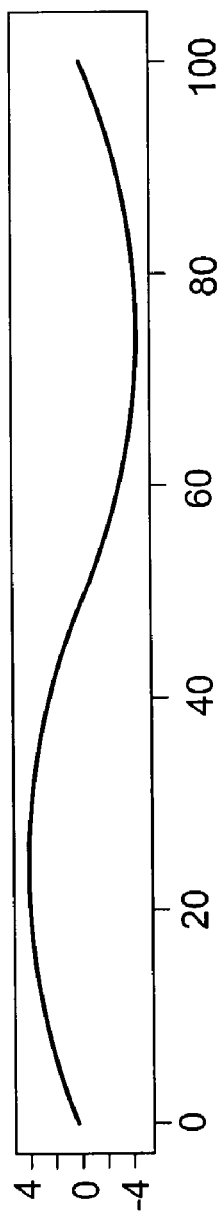
FIGS. 5a-5c illustrate graphs of airflow at particular points of the airflow passage.
Figure 5B:
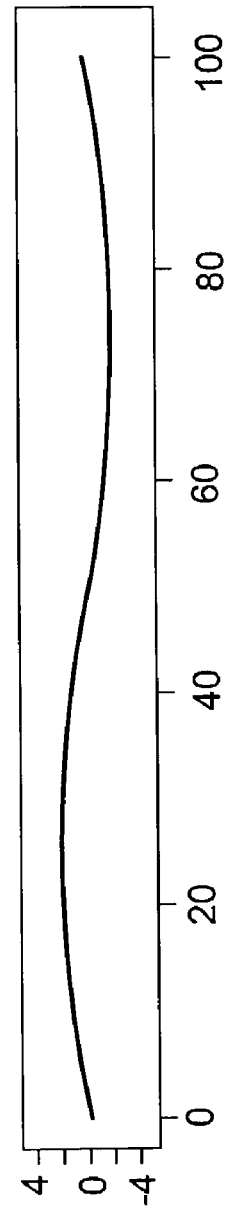
Figure 5C:
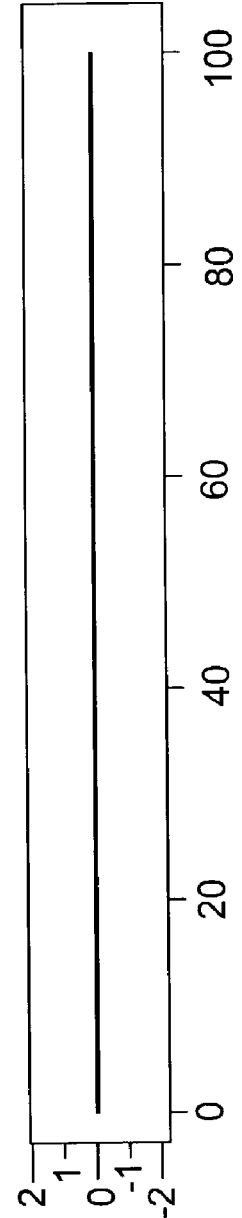

Unlike some conventional PAP system which adjust pressure to provide assisted breathing (i.e., to overcome respiratory effort), the system 1 is intended to maintain a substantially constant pressure $C_P$ in the segment CD, as shown in FIGS. 4c and 5c, to prevent as far as possible any assistance to or hinderance of the patient's breathing. By properly selecting $C_P$, airway collapse can be prevented without additional effect on breathing effort. The desired pressure in the segment CD is determined based on conditions of a particular patient. To maintain the pressure C, in the segment CD, the pressure $P_A$ (as shown in FIG. 5a) needs to be adjusted to compensate for dissipation of pressure along the segments AB and BC which precede the segment CD because they are upstream of the flow during inspiration and which add to the pressure generated during expiration because they are downstream of the flow. For example, the pressure $P_A$ might be adjusted to compensate for pressure dissipation in the segment AB during inspiration, as shown in FIG. 4a, due to the intrinsic resistance of the tube 21 and/or the mask 20. For example, during inspiration, the pressure $P_A$ is reduced by the time is reaches the mask 20 (see FIG. 5b). The pressure $P_A$ may be further adjusted to compensate for pressure dissipation in the segment BC, as shown in FIG. 4b. No adjustments are needed for pressure dissipation in the segment DE (see FIG. 4d).

A value of this pressure dissipation is determined by the resistance and the flow through each segment. This value may be either positive (e.g., during inspiration as shown in FIG. 3a) or negative (e.g., during expiration as shown in FIG. 3b). The pressure $C_P$ may be adjusted manually (e.g., by a technician performing a titration under laboratory monitoring) or automatically (e.g., by an automated self-titrating technique).

The pressure $P_A$ may be continuously determined according to the following exemplary formula:

$$P_A = C_P + R_{AB} * F_S + R_{BC} * F_P$$

wherein, $P_A$ is a pressure applied by the flow generator 22;

$C_P$ is the constant pressure which is targeted as that to be applied to the segment CD;

$R_{AB}$ is the resistance in the segment AB (which determines the pressure dissipation in the segment AB at each rate of airflow through the system);

$R_{BC}$ is a resistance in the segment BC (which determines the pressure dissipation in the segment BC at each rate of airflow in that segment);

$F_P$ is the instantaneous rate of flow of air by the patient (i.e., the actual flow rate in and out of the nose at each point of time of the patient's breathing (which is zero between breaths, rises throughout inspiration, then falls to zero and becomes negative during expiration) to which must be added any flow that occurs due to the leaks through the patient's mouth; and $F_S$ is an instantaneous rate of flow of air leaving the pressure generator 22 and flowing through the tube 21 to the patient (i.e., an actual flow rate at the inlet of the tube at each point of time). This rate of flow is composed of the flow rate of the patient's breathing (which is zero between breaths and rises throughout inspiration, then falls to zero and becomes negative during expiration), to which is added any amount of airflow leaking continuously through the system (which is composed of the sum of the flow of through the intentional leakport, any variable leaks present where the mask 20 fits to the patient's face and any leak though the patient's mouth).

The resistance (or rate of pressure dissipation) $R_{AB}$ for any given airflow circuit may be determined based on a measurement of the pressure $P_A$ which occurs when a particular flow rate X is used to calibrate the system 1. This calibration may be done with the distal end of the segment AB left open to the atmosphere and a known (either constant or varying) flow applied by the flow generator 22. Preferably, this applied flow should be approximately equivalent to an amount of leakage that will occur when the mask 20 is worn by the patient (e.g., 30 l/min). For example, this relationship defining the resistance $R_{AB}$ may be a substantially constant ratio of $F_S$ to $P_A$. Those skilled in the art will understand that the $R_{AB}$ may be different as various tubes and masks are used as the tube 21 and the mask 20, respectively. The determination of the $R_{AB}$ value may require a calibration phase during which flow from the flow generator 22 is systematically varied through a full range of possible flows (e.g., 0-50 l/min), while no patient is attached to the segment AB. Alternatively, the $R_{AB}$ value may be obtained from a table of previously calculated data for the pressure/flow relationship for a particular segment AB (e.g., a known tube/mask combination).

The $R_{BC}$ and the resultant correction value for a loss of pressure within the segment BC of the patient's airway which is upstream of the collapsible segment CD of the upper airway is more difficult to determine directly from measurements external to the patient. In normal patients, the resistance of the upper airway is known from published data (using direct measurement by rhinometry) to be about 0.1-0.2 cm $H_2O$/liter/sec of flow.

In the absence of direct patient data, a fixed value of the $R_{BC}$ (e.g., in the vicinity of 0.1 cm $H_2O$/liter/sec) may be assumed if the patient has no nasal disease. Higher values could be assumed if there is, by clinical history or patient examination, a known pathology of the nose expected to produce an increase in nasal resistance. If rhinometry of the patient is performed prior to use of the system 1, the value obtained may be used as the pressure dissipation value $R_{BC}$.

Once the $R_{BC}$ and $R_{AB}$ have been estimated or determined, the values of $R_{AB}$ is multiplied by $F_S$ and $R_{BC}$ is multiplied by $F_P$ and these values are summed. This result is continuously updated to regularly compensate for the loss or addition of pressure in the segments AB and BC. The value of $F_S$ is the measured flow exiting the flow generator 22, and the value of $F_P$ (the patient's instantaneous flow rate) plus any leak through the patient's mouth may be determined by averaging a value of flow of the flow measured exiting of the flow generator 22 over multiple respiratory cycles and subtracting this average value from an instantaneous flow value from the flow generator 22. This calculation results in the patient's instantaneous flow because the patient's inhalation and exhalation volumes must be equal, and thus the weighted time averages of the patient's flow rate over multiple respiratory cycles must be zero. Thus, any non-zero value of the average system flow from the flow generator 22 must be due to leaks which are not part of the patient's respiration flow. If this average system flow is subtracted from the total flow, what remains is an instantaneous patient flow (which averages over time to zero).

As stated above, the system 1 avoids the problems associated with systems that intentionally or unintentionally assist the breathing of patients by providing different pressures to the patient's lungs during inhalation and exhalation. Specifically, these systems may cause patients to inhale more air than they require inducing a reaction whereby the patient draws less air in subsequent breaths relying on the system assist to provide the extra air required. The system may then react by changing the inhalation and exhalation pressures and a series of system adjustments and patient reactions may be begun which, in some cases, is never stabilized. By maintaining the pressure in the collapsible portion of the airway substantially constant, the patient receives no breathing assistance and these problems are not encountered. The only variations in pressure are above the collapsible segment of the airway and do not extend below in such a way as to reach the lung itself. Thus, at no time does the present system deliver a pressure which would assist the patient's normal breathing efforts or reduce his efforts below that which would be present if he had no disease of his upper airway and were breathing without the mask.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A system for treatment of a sleeping disorder, comprising:
   a flow generator supplying a pressurized airflow to an airway of a patient; and
   a processing arrangement connected to the flow generator to control a supply pressure at which the airflow is generated by the flow generator, wherein the processing arrangement continuously adjusts the supply pressure to maintain a pressure in a predetermined portion of the patient's airway substantially constant.

2. The system according to claim 1, wherein the predetermined portion of the patient's airway includes a collapsible portion of an upper airway of the patient and wherein the processing arrangement controls the supply pressure to maintain the pressure in the collapsible portion of the patient's airway at a predetermined value.

3. The system according to claim 2, wherein the predetermined value is at least as great as a tissue pressure below which the collapsible portion collapses.

4. The system according to claim 2, wherein the pressure is maintained substantially constant in the predetermined portion throughout one of an entire inspiratory phase and a full respiratory cycle.

5. The system according to claim 2, further comprising:
   a mask situated over at least one of a mouth and a nose of the patient; and
   a tube providing the airflow from the flow generator to the mask.

6. The system according to claim 5, further comprising:
   a venting arrangement diverting gases exhaled by the patient from the incoming airflow to prevent re-breathing of the exhaled gases.

7. The system according to claim 6, wherein the venting arrangement includes at least one of a leak port and a non-rebreathing valve with a venting tube.

8. The system according to claim 5, wherein the supply pressure is determined according to the following formula:

$$P_A = C_P + R_{AB}*F_S + R_{BC}*F_P$$

wherein,
$P_A$ is the supply pressure provided by the flow generator;
$C_P$ is the pressure to be applied to the collapsible portion of the airways;
$R_{AB}$ is a resistance in a first portion of the airways;
$F_S$ is a value of a total flow rate through the system at each point in time;
$R_{BC}$ is a resistance in a second portion of the airways; and
$F_P$ is a value of an instantaneous flow rate of a patient's breathing,
wherein the first portion is located between (i) the flow generator and (ii) one of the nose and the mouth of the patient, and wherein the second portion is located between (i) one the nose and the mouth of the patient and (ii) the predetermined portion.

9. The system according to claim 8, further comprising:
a first sensor measuring a first value of the airflow in the tube and providing the measured data to the processing arrangement.

10. The system according to claim 9, further comprising:
a second sensor measuring a first pressure in one of the mask and the flow generator, the second sensor providing the measured data to the processing arrangement.

11. The system according to claim 10, wherein the value of $R_{AB}$ is determined when the flow generator is providing the airflow and the mask is opened to atmosphere, the value $R_{AB}$ being determined as a function of the first value and the first pressure.

12. A method for treating a sleeping disorder, comprising the steps of:
supplying a pressurized airflow to an airway of the patient; and
controlling a supply pressure at which the airflow is supplied to the patient's airway so that a pressure in a predetermined portion of the patient's airway is maintained substantially constant.

13. The method according to claim 12, wherein the predetermined portion of the patient's airway includes a collapsible portion thereof and wherein the supply pressure is controlled to maintain the pressure within the collapsible portion at a predetermined value.

14. The method according to claim 13, wherein the predetermined value is at least as great as a tissue pressure below which the collapsible portion collapses.

15. The method according to claim 13, wherein the pressure is maintained substantially constant in the predetermined portion throughout one of an entire inspiratory phase and a full respiratory cycle.

16. The method according to claim 13, further comprising the steps of:
generating the airflow using a flow generator; and
providing the airflow to a mask situated over at least one of a nose and a mouth of the patient via the tube.

17. The method according to claim 16, further comprising the step of:
diverting gases exhaled by the patient from the incoming airflow, by a venting arrangement, to prevent re-breathing of the exhaled gases.

18. The method according to claim 16, further comprising the step of:
with the processing arrangement, determining the supply pressure according to the following formula:

$$P_A = C_P + R_{AB} * F_S + R_{BC} * F_P$$

wherein,
$P_A$ is the supply pressure provided by the flow generator;
$C_P$ is the pressure to be applied to the collapsible portion of the airways;
$R_{AB}$ is a resistance in a first portion of the airways;
$F_S$ is a value of a total flow rate through the system at each point in time;
$R_{BC}$ is a resistance in a second portion of the airways; and
$F_P$ is a value of an instantaneous flow rate of a patient's breathing.

19. The method according to claim 18, further comprising the steps of:
using a first sensor, measuring a first value of airflow in the tube; and
providing the measured data to the processing arrangement.

20. The method according to claim 19, further comprising the steps of:
using a second sensor, measuring a first pressure in one of the flow generator and the mask; and
providing the measured data to the processing arrangement.

21. The method according to claim 20, further comprising the step of:
when the flow generator is providing the pressurized airflow and the mask is opened to atmosphere, determining the value of $R_{AB}$ as a function of the first value and the first pressure.

22. A system for treatment a sleeping disorder, comprising:
a flow generator generating a pressured airflow;
a mask situated over at least one of a mouth and a nose of a patient to provide the pressurized airflow to an airway of a patient;
a tube providing the airflow from the flow generator to the mask; and
a processing arrangement connected to the flow generator to control a supply pressure at which the airflow is generated by the flow generator,
wherein the processing arrangement continuously adjusts the supply pressure to maintain a pressure in a collapsible portion of an upper airway of the patient substantially constant, the pressure being at a value at least as great as a tissue pressure below which the collapsible portion collapses,
wherein the supply pressure is determined according to the following formula:

$$P_A = C_P + R_{AB} * F_S + R_{BC} * F_P$$

wherein,
$P_A$ is the supply pressure provided by the flow generator;
$C_P$ is the pressure to be applied to the collapsible portion of the airways;
$R_{AB}$ is a resistance in a first portion of the airways;
$F_S$ is a value of a total flow rate through the system at each point in time;
$R_{BC}$ is a resistance in a second portion of the airways; and
$F_P$ is a value of an instantaneous flow rate of a patient's breathing,
wherein the first portion is located between (i) the flow generator and (ii) one of the nose and the mouth of the patient, and
wherein the second portion is located between (i) one the nose and the mouth of the patient and (ii) the predetermined portion.

* * * * *